United States Patent [19]

Vanlerberghe et al.

[11] 3,953,608

[45] Apr. 27, 1976

[54] COSMETIC COMPOSITIONS FOR THE SKIN CONTAINING A CHITOSAN DERIVATIVE

[75] Inventors: Guy Vanlerberghe, Montjay-la-Tour; Henri Sebag, Paris, both of France

[73] Assignee: L'Oreal, Paris, France

[22] Filed: Sept. 11, 1974

[21] Appl. No.: 504,953

Related U.S. Application Data

[62] Division of Ser. No. 251,263, May 8, 1972, Pat. No. 3,879,376.

[30] Foreign Application Priority Data

May 10, 1971  Luxemburg............................ 63142

[52] U.S. Cl............................ 424/361; 260/211 R; 424/47; 424/73; 424/81; 424/170; 424/172; 424/365

[51] Int. Cl.$^2$.......................................... A61K 7/48

[58] Field of Search............ 260/211 R; 424/DIG. 1, 424/DIG. 2, 47, 361, 365, 73, 81, 170, 172

[56] References Cited

UNITED STATES PATENTS

| | | | |
|---|---|---|---|
| 2,702,249 | 2/1955 | Baird................................ | 260/211 R |
| 3,014,027 | 12/1961 | Druey et al....................... | 260/211 R |
| 3,133,912 | 5/1964 | Kimig et al....................... | 260/211 R |
| 3,251,824 | 5/1966 | Batista............................. | 260/211 R |
| 3,478,015 | 11/1969 | Oneshi et al.................... | 260/211 R |

*Primary Examiner*—Stanley J. Friedman
*Assistant Examiner*—Vera C. Clarke
*Attorney, Agent, or Firm*—Cushman, Darby & Cushman

[57] ABSTRACT

Chitosan derivatives formed by acylation of chitosan with a saturated or unsaturated organic diacid anhydride are employed as a skin moisturizing agent in a cosmetic composition comprising an aqueous solution containing 0.1–20 percent by weight of said chitosan derivative.

8 Claims, No Drawings

COSMETIC COMPOSITIONS FOR THE SKIN CONTAINING A CHITOSAN DERIVATIVE

This is a division of application Ser. No. 251,263 filed May 8, 1972, now U.S. Pat. 3,879,376.

The present invention relates to novel macromolecular compounds derived from chitosan which present particularly advantageous properties as filmogens, as sequestrants of ions of heavy metals such as iron and copper and as skin moisturizing agent for incorporation into cosmetic compositions.

Chitosan is a product of the deacetylation of chitin, a natural polyglucosamine whose amine groups are acetylated and which is found in certain mushrooms and the sheels of crustacea.

Since deacetylation of chitin by alkaline reagents cannot be performed completely, chitosan, which serves as the starting product for compounds of the invention, comprises in its molecule both free amine residues and acetylamine residues. The degree of deacetylation of chitin is evaluated by determining by titration the percentage of free base of the molecule, which is generally located below 95%.

Chitosan is, by the presence of these free amine groups, a cationic polymer, which presents the major drawback of being insoluble in an alkaline medium.

Known derivatives of chitosan, obtained by alkylation of this compound, hardly differ from chitosan itself as far as their alkaline solubility is concerned.

To improve this property of chitosan, the applicants have tried to make its molecule undergo other modifications. The difficulties encountered in these attempts are explained principally by the fact that chitosan is soluble only in an acid medium, in the form of salts. Further, it is known that it is generally very difficult to achieve condensation or addition reactions on amine salts. The applicants have now developed a process which makes it possible to acylate chitosan. Thus, the present invention relates to chitosan derivatives obtained by the acylation of this compound by means of saturated or unsaturated organic diacid anhydrides, followed if desired in the case of unsaturated anhydrides, by the addition on the double bonds of compounds with primary or secondary amine groups to provide other functional substituents.

The novel compounds according to the invention are polymers having monomer patterns of the formula

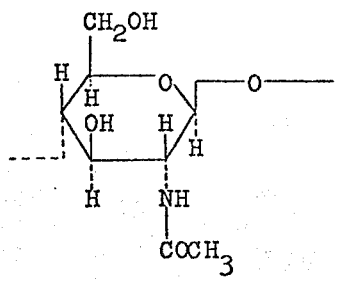

(A)

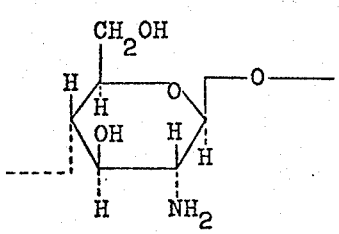

(B)

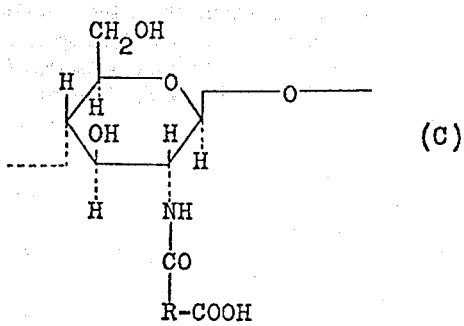

(C)

scattered randomly in the molecule of the polymer, the numerical proportions of these three patterns being respectively 5 to 30% for A, 5 to 40% for B and 30 to 90% for C.

In formula C, R represents a member selected from the group consisting of the formula

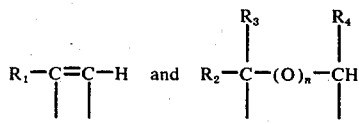

wherein $R_1$ is selected from the group consisting of hydrogen and methyl and $n$ is equal to (a) O, in which case $R_2$, $R_3$ and $R_4$ each independently represent a member selected from the group consisting of hydrogen; methyl; hydroxyl; acetoxy; amino; monoalkylamino wherein the alkyl moiety has 1 to 12 carbon atoms or dialkylamino wherein the alkyl moiety has 1 to 3 carbon atoms, said monoalkylamino and dialkylamino being optionally substituted by one or more amine, hydroxyl, mercapto, carboxyl, alkylthio wherein the alkyl moiety has 1 to 8 carbon atoms or sulfonic groups; alkylthio wherein the alkyl moiety has 1 to 4 carbon atoms and carries an amine residue; and a residue of an oligopeptide such as glutathion or a product of protein hydrolysis, one at least of radicals $R_2$, $R_3$ and $R_4$ being a hydrogen atom and radicals $R_2$ and $R_3$ being able, in addition, to form together a methylene radical; and to (b) 1, in which case $R_2$, $R_3$ and $R_4$ each represent hydrogen.

The acid and base groups which appear in the molecules of the polymers according to the invention are able to be ionized in an aqueous solution, thus yielding salts either between two patterns B and C, or in the same pattern C.

These same ionized forms also appear in the presence of inorganic or organic bases and acids. The salts formed with these acids or bases are, of course, also a part of the invention.

These salts can be obtained with acids such as, for example, hydrochloric, phosphoric, acetic, lactic, tartaric or citric acid or alternatively with bases such as sodium hydroxide, potassium hydroxide, ammonia, lime, magnesia, alkanolamines such as triethanolamine, triisopropanolamine, aminomethylpropanol, or aminomethylpropanediol, or with amino acids and more particularly amino acids of a base nature such as lysine or arginine.

The compounds according to the invention are prepared, according to a process developed by the applicants, by acylating the chitosan by means of a saturated or unsaturated anhydride of the formula

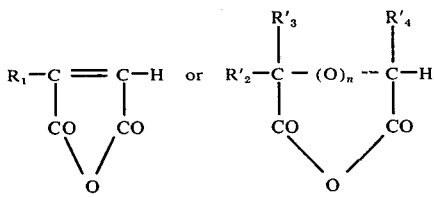

wherein $R_1$ has the meaning given above and wherein when $n$ is equal to O, $R'_2$, $R'_3$ and $R'_4$ each independently represent hydrogen, methyl or acetoxy with the proviso that at least one of these radical is hydrogen and radicals $R'_2$ and $R'_3$ can further form together a methylene residue; and wherein when $n$ is equal to 1, $R'_2$, $R'_3$ an $R'_4$ each represent hydrogen, after which, in the case where an unsaturated anhydride is used, the product obtained can be subjected to an addition reaction with at least a primary or secondary amine whose hydrocarbon residue can be interrupted by one or more nitrogen atoms and/or substituted by one or more amine, hydroxyl, carboxyl, sulfonic or mercapto residues.

The chitosan acylation reaction is performed by adding to an aqueous solution of a chitosan salt, having a concentration of 1 to 20 weight percent thereof, alternately and by fractions, on the one hand, a base diluted solution intended to release amine functions of the chitosan and to salify the acid formed, and, on the other hand, the anhydride defined above. The reaction is performed between 10° and 50°C and preferably between 15° and 30°C, by using 0.3 to 2 moles of a saturated anhydride per equivalent of amine present in the chitosan, or 1 to 2 moles of unsaturated anhydride per equivalent of amine present in the chitosan. The anhydride can be used in this reaction either in powder form or in the form of a solution in an inert solvent such as, for example, dioxane, tetrahydrofuran or ethyl acetate.

Since the addition of the base causes partial precipitation of the chitosan, this reaction is performed in a heterogeneous medium. Further, since the anhydrides are unstable compounds in water, they can hydrolyze into the corresponding diacids, giving rise to a secondary reaction. However, despite these unfavorable conditions, the rate of acylation, computed from the acid number corresponding to this secondary reaction, is generally greater than 70%.

The chitosan salts used in this acylation reaction are, for example, the hydrochloride or acetate, while the bases can be sodium or potassium hydroxide, or again, and preferably, acid or neutral carbonates of sodium or potassium.

The saturated anhydrides used can be, for example, succinic anhydride, acetoxy succinic anhydride, methylsuccinic anhydride, diacetyl tartaric anhydride or diglycolic anhydride. The unsaturated anhydrides used can be, for example, maleic anhydride, itaconic anhydride or citraconic anhydride.

In the case where the starting anhydride is unsaturated, this acylation reaction can be followed by an addition reaction which makes it possible to achieve a range of quite varied products.

The addition reactions according to the invention can for the most part be performed at a pH above 7 and at a temperature between 20°C and 60°C for several hours. Advantageously the reaction is carried out in a nitrogen atmosphere.

The amino reagents, used in these reactions, are present in a proportion of 0.1 to 10 moles per unsaturated pattern, this proportion being a function of the properties desired. Thus, for example, in the case of polyfunctional reagents it is possible to obtain, as a function of this number of moles, mobile, clear solutions, gels or compounds that are no longer soluble in water because of too great a reticulation.

The reagents used in the addition reactions according to the invention can be ammonia; mono- or polyamines such as methylamine, ethylamine, propylamine, butylamine, hexylamine, octylamine, dimethylamine, diethylamine, ethylenediamine, hexamethylenediamine, diethylenetriamine, triethylenetetramine and tetraethylenepentamine; alkanolamines such as monoethanolamine, isopropanolamine and diethanolamine; mercapto-amines such as $\beta$-mercapto ethylamine; amines with acid functions such as glycocoll, alanine, leucine, isoleucine, valine, aspartic acid, glutamic acid, serine, lysine, cysteine, methionine, cysteic acid, penicillamine, and methyltaurine; or again more complex compounds comprising polypeptidic linkings as glutathion and protein hydrolyzates. When a mercapto-amine is used, the addition on the double bond can also be made by the amine group or mercapto group.

For the preparation of the compounds according to the invention, it is desirable to use chitosan comprising from 70 to 95% of free amine groups. The percentage of these amine groups can be determined, in a known way, by dissolving of a sample in a known and excessive amount of hydrochloric acid which is determined back by a soda solution.

The chitosan that can be used for the purposes of the invention can also be selected as a function of the viscosity of their solutions. Ths viscosity of their solutions at 2 in 3% acetic acid, measured at 25°C after 24 hour can vary from 3 to 130 centipoises.

All the compounds obtained according to the process of the invention can be precipitated from their aqueous solution by modification of the pH and/or by addition of a solvent such as alcohol or acetone. Further, they can be isolated by other processes such as dialysis or passage over an ion exchange resin.

The compounds according to the invention are soluble in alkaline medium. The precipitate for the most part between pH 4 and pH 6; some of them are soluble in an excess of acid.

The compounds according to the invention constitute polyampholytes which present particularly advantageous properties in regard to filmogens and sequestrants of heavy metal ions.

Actually, the compounds of the invention present a particularly marked sequestering action with regard to ions of heavy metals, such as iron and copper, and in particularly slight concentrations. These ions, which generally come from water in take pipes, are particularly bothersome in certain industrial sections because they give rise to the formation of precipitates and they accelerate oxidation reactions. Thus, their elimination is particularly desirable.

Further, the compounds according to the invention remain in solution in the presence of alkaline earth ions, which advantageously differentiates them from natural polymers, such as alginates, which precipitate in an aqueous solution in the presence of these ions.

The combination of these two properties permits the compounds of the present invention to find a particularly interesting application as sequestrants of heavy metal ions in the food, pharmaceutical and textile industries. Their sequestering property in the presence of alkaline earth ions also makes it possible to use them in detergent compositions. Their ampholyte character makes it possible to associate them indifferently with cationic, anionic and, of course, non-ionic detergents. In these applications, they present, in relation to usual sequestrants such as EDTA, the advantage of being able to be used in clearly smaller proportions.

The compounds according to the invention further have filmogen properties. Actually, they give, on evaporation of their aqueous solution, perfectly transparent films, which are relatively hard and not sticky, and which can be plastic or brittle, depending on the particular compound selected. Further, the films are capable of exchanging water vapor with the surrounding environment without losing their film characteristics.

This property, joined to the characteristic, which most of the compounds according to the invention present, of precipitating from their aqueous solutions at a pH between pH 4 and pH 6, i.e., in the pH zone of the sin, has a very interesting application in cosmetic or pharmaceutical preparations intended to moisten the skin or give it natural constituents.

The present invention also relates to cosmetic compositions comprising an aqueous solution of at least one of the compounds according to the present invention in amounts of 0.1 to 20% by weight and preferably from 0.25 to 10% by weight.

The cosmetic compositions of this invention also contain, besides the novel chitosan derivatives, thickening or agglutinating agents such as carboxyvinyl polymers marketed by the Goodrich Chemical Company under the tradename Carbopol, softening agents such as lanolin, fatty acid esters known in cosmetology such as glycerin monostearate, Pur Cellin oil, preservatives, perfumes and the like.

These cosmetic compositions can be in the form of creams, lotions, gels, as well as in the form of oils or aerosols.

The novel chitosan derivatives of this invention can be used in the preparation of bath products and deodorants.

The following examples are given to illustrate the present invention.

EXAMPLE A

Preparation of the product of condensation of chitosan with maleic anhydride (compound No. 10).

To 20 g of chitosan, having a viscosity of 3.5 cps (96 milliequivalents in amine groups), dispersed in 200 ml of water, there are added 8 ml of concentrated hydrochloric acid to neutralize exactly the free amine functions, with stirring to complete dissolving. If necessary, the undissolved chitosan particles can be filtered therefrom.

Then there are added at room temperature, alternately and in four equal fractions, on the one hand, 164 g (192 meq) of a sodium bicarbonate solution at 1.16 meq/g, and, on the other hand, 9.4 g (96 millimoles) of maleic anhydride powder. Addition of each fraction takes 5 to 10 minutes, the interval of introduction between two fractions being 30 to 45 minutes.

When the reaction is completed, the acid number is measured and is determined to be 0.03 meq/g, which corresponds to a total acidity of 12.5 meq.

The amount of base introduced is the stoichiometric amount necessary to neutralize both the hydrochloric acid used to make the chitosan salt and the maleamic acid formed.

The total acidity therefore takes into account the secondary reaction of hydrolysis. The rate of reaction is $$\frac{12.5 \times 100}{96} = 13\%,$$

and consequently the rate of condensation of maleic anhydride on chitosan is 87%.

The compound thus prepared is isolated in acid form by adding 190 ml of normal hydrochloric acid. The resulting precipitate is filtered, drained, washed first with water and then with acetone, and dried.

The perfectly dry product can be ground and is in the form of a very slightly tinted white powder.

Other compounds are prepared according to the same mode of operation. The starting products and reaction conditions are given in Table I below.

TABLE I

| Polymer reactant | Conc. of polymer | Condensation reactant | Molar proportions | Temp °C. | Reaction time (hrs) | Precipitation Solvent | Compound No. |
|---|---|---|---|---|---|---|---|
| Chitosan (3.5 cps) | 5% | maleic anhydride | 1 | 20 | 3–4 | water (HCl) | 10 |
| Chitosan (33 cps) | 3.5% | maleic anhydride | 1 | 20 | 3–4 | water (HCl) | 20 |
| Chitosan (117 cps) | 2% | maleic anhydride | 1 | 20 | 3–4 | water (HCl) | 30 |

TABLE I -continued

| Polymer reactant | Conc. of polymer | Condensation reactant | Molar proportions | Temp °C. | Reaction time (hrs) | Precipitation Solvent | Compound No. |
|---|---|---|---|---|---|---|---|
| Chitosan (3.5 cps) | 5% | itaconic anhydride | 1 | 20 | 3–4 | ethyl alcohol | 40 |
| Chitosan (33 cps) | 3.5% | itaconic anhydride | 1 | 20 | 3–4 | — | 50 |
| Chitosan (117 cps) | 2% | itaconic anhydride | 1 | 20 | 3–4 | ethyl alcohol | 60 |
| Chitosan (3.5 cps) | 5% | succinic anhydride | 0.5 | 20 | 3–4 | | 70 |
| Chitosan (117 cps) | 2% | succinic anhydride | 1 | 20 | 3–4 | ethyl alcohol | 90 |
| Chitosan (3.5 cps) | 4.5% | succinic anhydride | 1 | 25 | 8 | water (HCl) | 70 bis |
| Chitosan (33 cps) | 4.5% | succinic anhydride | 0.5 | 25 | 8 | water (HCl) | 80 |
| Chitosan (33 cps) | 3.5% | succinic anhydride | 1 | 25 | 8 | water (HCl) | 80 bis |
| Chitosan (3.5 cps) | 4.5% | citraconic anhydride | 1.2 | 25 | 8 | — | 100 |

EXAMPLE B

Preparation of the product of addition of compound No. 10 prepared in Example 1 with glycocoll.

There are dispersed 7 g of compound No. 10, or 20 meq, in 40 ml of water. Then 10 ml of 2N soda are added to neutralize and solubilize it. To the solution thus obtained there are added 1.5 g of glycocoll (20 meq) dissolved in 10 ml of 2N soda. The reaction mixture is then heated at 50°C for 1 hour, under a nitrogen atmosphere.

The compound thus obtained is soluble in an alkaline medium and an acid medium. It can be preserved in aqueous solution or isolated, by precipitation, either in the form of sodium salt by addition of ethyl alcohol, or at the isoelectric point by addition of hydrochloric acid, in an aqueous or dilute alcohol medium.

Other compounds, listed in Table II below, are prepared by the same mode of operation.

TABLE II

| Polymer reactant | Conc. of polymer | Addition reactant | Molar proportions | Temp °C. | Reaction time (hrs) | Precipitation Solvent | Compound No. |
|---|---|---|---|---|---|---|---|
| 10 | 12% | Ethanolamine | 1.2 | 60 | 5 | Ethanol | 11 |
| 10 | 10% | Glycocoll | 1 | 50 | 1 | — | 12 |
| 10 | 7% | Cysteine | 1 | 20 | 1 | Ethanol | 13 |
| 10 | 10% | Methionine | 1 | 60–90 | 10 | — | 14 |
| 10 | 8% | Methyl taurine | 1 | 50–70 | 9 | — | 15 |
| 20 | 10% | Ammonia | 3 | 50 | 120 | — | 21 |
| 20 | 12% | Methylamine | 3 | 20 | 24 | — | 22 |
| 20 | 10% | Dimethylamine | 1 | 20 | 20 | — | 23 |
| 20 | 5% | Diethanolamine | 1 | 60 | 60 | — | 24 |
| 20 | 10% | Glycocoll | 1 | 60 | 21 | — | 25 |
| 20 | 15% | Aspartic acid | 1 | 80 | 36 | — | 26 |
| 20 | 10% | Cysteine | 1 | 20 | 72 | — | 27 |
| 40 | 8% | Ethylenediamine | 0.14 | 90 | 3 | Acetone | 41 |
| 40 | 8% | Sarcosine | 10 | 35 | 24 | Ethanol | 42 |
| 40 | 5% | Serine | 1.5 | 60 | 20 | Ethanol | 43 |
| 40 | 5% | Cysteine | 1 | 50 | 5 | — | 44 |
| 10 | 18% | Glutamic acid | 1 | 55–60 | 10 | Water (HCl) | 16 |
| 10 | 10% | Aspartic acid | 1 | 25 | 10 | Water (HCl) + Ethanol | 17 |
| 10 | 12% | Leucine | 1 | 25 | 24 | Ethanol | 18 |
| 10 | 4% | Tyrosine | 1 | 80–85 | 5 | | 19 |
| 10 | 10% | Tryptophane | 1 | 25 | 70 | Ethanol | 11 A |
| 10 | 4.5% | Glutathion* | 1.2 | 25 | 24 | Ethanol | 12 A |
| | | Penicill- | | | | | |

TABLE II-continued

| Polymer reactant | Conc. of polymer | Addition reactant | Molar proportions | Temp °C. | Reaction time (hrs) | Precipitation Solvent | Compound No. |
|---|---|---|---|---|---|---|---|
| 10 | 5% | amine** | 1.1 | 25 | 72 | Ethanol | 13 A |

*For condensation, only one acidity of the two of the Glutathion is neutralized.
**The Penicillamine is solubilized in acid form in water and is reacted in this form.

The following examples illustrate embodiments of cosmetic compositions containing the compounds of the present invention.

EXAMPLE 1

A softening cleansing milk is prepared having the following composition in % by weight:

| | |
|---|---|
| Polyoxyethylene stearate | 3.0 |
| Glycerin monostearate (Arlacel 165) | 3.0 |
| Vaseline oil | 36.2 |
| Self emulsifiable Pur Cellin oil | 2.0 |
| Lanolin | 2.0 |
| Carboxyvinyl polymers (Carbopol 941) | 0.1 |
| Triethanolamine | 0.13 |
| Compound No. 70 bis | 0.6 |
| Rose water | 3.0 |
| Preservative (methyl p-hydroxybenzoate) | 0.3 |
| Perfume | 0.2 |
| Demineralized water, sufficient for | 100% |

The fatty components (polyoxyethylene stearate, glycerin monostearate, vaseline oil, Pur Cellin oil and lanolin) are melted. This mixture is then added to a solution of Carbopol 941 obtained by dissolving the Carbopol in one part of water and then neutralizing it with triethanolamine. An emulsion of the above components is then formed by stirring well.

Compound No. 70 bis is carefully dispersed in the rest of the water and neutralized by triethanolamine. Then the rose water, in which the preservative is dissolved, is added.

Finally, the preceding emulsion is diluted with the solution obtained with compound No. 70 bis and the whole is perfumed.

When applied to the skin, this milk gives an impression of freshness and softness.

EXAMPLE 2

A hydrating and protective cleansing base is prepared according to the same mode of operation as for the milk of Example 1, said base having the following composition in % by weight:

| | |
|---|---|
| Stearic acid | 2.0 |
| 2,6,10,15,19,23-hexamethyltetracosane (perhydrosqualene) $C_{30}H_{62}$ | 20.0 |
| Glycerin monostearate (Arlacel 165) | 2.0 |
| Triethanolamine | 1.0 |
| Methyl parahydroxybenzoate | 0.3 |
| Carboxyvinyl polymers (Carbopol 941) | 0.3 |
| Triethanolamine | 0.3 |
| Compound No. 70 bis | 1.0 |
| Perfume | 0.3 |
| Demineralized water, sufficient for | 100% |

This base has a good spreading power and assures a good protection to the skin.

EXAMPLE 3

According to the same mode of operation as for the milk of Example 1, there is prepared a softening cream for legs that have undergone depilation, said cream having the composition by weight in % of:

| | |
|---|---|
| Fatty acid ester (Pur Cellin oil) | 2.0 |
| Vaseline oil | 7.0 |
| Isopropyl myristate | 1.5 |
| 2,6,10,15,19,23-hexamethyltetracosane (perhydrosqualene) $C_{30}H_{62}$ | 3.5 |
| Lanolin Alcohols (Amerchol L 101) | 0.3 |
| Stearic acid | 1.4 |
| Glycerin monostearate | 2.0 |
| Hexadecylic alcohol | 1.0 |
| Pure cetyl alcohol | 0.2 |
| Preservative (methyl-p-hydroxybenzoate) | 0.3 |
| Carboxyvinyl polymers (Carbopol 941) | 0.25 |
| Triethanolamine | 0.25 |
| Perfume | 0.2 |
| Triethanolamine | 0.7 |
| Compound No. 10 | 2.5 |
| Demineralized water, sufficient for | 100% |

When applied to the skin, this cream gives it an impression of softness.

EXAMPLE 4

According to the same mode of operation as for the milk of Example 1, a hand cream is prepared with the composition in % by weight:

| | |
|---|---|
| Paraffin oil | 20.0 |
| Stearic acid | 6.0 |
| Triethanolamine | 3.0 |
| Glycerol monostearate | 2.0 |
| Soybean lecithin | 1.0 |
| Compound No. 10 | 3.0 |
| Perfume | 0.2 |
| Preservative (methyl-p-hydroxybenzoate) | 0.3 |
| Water, sufficient for | 100% |

This cream is very penetrating and imparts good suppleness to the skin shortly after its application thereto.

EXAMPLE 5

Preparation of an after-shave gel.

This gel having the following composition in % by weight:

| | |
|---|---|
| Compound No. 80 | 0.25 |
| Carbopol 934 | 0.25 |
| Triethanolamine | 0.375 |
| Propylene glycol | 5.0 |
| Preservative (methyl-p-hydroxybenzoate) | 0.3 |
| Perfume | 0.2 |
| Water, sufficient for | 100% | is prepared as follows:

A solution of compound No. 80 obtained by dispersing said compound in one part of water and neutralized with triethanolamine is mixed with Carbopol 934 neutralized with triethanolamine in propylene glycol. The preservative dissolved in water is then added to the whole. Perfume is then added to the resulting mixture.

This gel, when applied to the skin, gives it a feeling of freshness.

EXAMPLE 6

Preparation of a body cream with the composition in % by weight:

| | |
|---|---|
| Vaseline oil | 9.5 |
| Oleyl alcohol | 1.0 |
| Glycerol monostearate | 1.0 |
| Stearic acid | 1.0 |
| Carboxyvinyl polymers (Carbopol 941) | 0.15 |
| Triethanolamine | 0.65 |
| Propylene glycol | 2.0 |
| Preservative | 0.3 |
| Compound No. 10 | 0.4 |
| Demineralized water, sufficient for | 100% |

The following operation is followed:

The fatty components and the preservative are mixed and this phase is poured into the Carbopol gel containing one part water, triethanolamine and propylene glycol. It is then emulsified for 10 minutes.

The cream thus obtained is diluted with a solution of compound No. 10 neutralized wih triethanolamine, in 30 ml of demineralized water. It is finally cooled to 25°C. This cream spreads very easily and gives the skin a feeling of softness.

EXAMPLE 7

Preparation of a hydrating lotion.

This lotion having the following composition in % by weight:

| | |
|---|---|
| Hamamelis water | 50.0 |
| Compound No. 80 | 1.0 |
| Aminomethylpropanol | 0.3 |
| Preservative (methyl-p-hydroxybenzoate) | 0.3 |
| Perfume | 0.2 |
| Water, sufficient for | 100% | is prepared as follows:

The preservative is dissolved in water. Compound No. 80 is dispersed in one part of water and aminomethylpropanol is dissolved in the remaining water. The resulting three solutions are mixed and neutralized with aminomethylpropanol. The hamamelis water and perfume are then added. This lotion, when applied to the skin, gives it a feeling of freshness.

EXAMPLE 8

Preparation of a protective beauty cream.

| | |
|---|---|
| Composition in % by weight: | |
| Paraffin oil | 15.0 |
| Stearic acid | 5.0 |
| Triethanolamine | 2.5 |
| Cetyl alcohol | 3.0 |
| Compound No. 10 | 2.0 |
| Perfume | 0.2 |
| Preservative (methyl-p-hydroxybenzoate) | 0.3 |
| Water, sufficient for | 100% |

EXAMPLE 9

A perfumed bath oil of the composition in % by weight is prepared:

| | |
|---|---|
| Propylene glycol | 8.0 |
| Isopropyl myristate | 1.0 |
| Compound No. 70 bis | 10.2 |
| Perfume | 0.2 |
| Preservative (methyl-p-hydroxybenzoate) | 0.3 |
| Water, sufficient for | 100% |

Compound No. 70 bis is dissolved in water, after neutralization with aminomethylpropanol, then the other ingredients of the formula are added.

EXAMPLE 10

A bath cream of the composition in % by weight is prepared:

| | |
|---|---|
| Paraffin oil | 40.0 |
| Cetyl stearyl alcohol | 3.0 |
| Sorbitan monostearate | 3.0 |
| Polyoxyethylene sorbitan monolaurate | 4.0 |
| Compound No. 70 bis | 4.0 |
| Perfume | 0.2 |
| Preservative (methyl-p-hydroxybenzoate) | 0.3 |
| Water, sufficient for | 100% |

The novel chitosan derivatives can also enter into the composition of filmogeneous products such as preparations for coloring the skin, deodorizing products and antispot products.

As examples there can be cited:

EXAMPLE 11

A filmogeneous product of the composition in % by weight is prepared:

| | |
|---|---|
| Compound No. 70 bis | 3 |
| Triethanolamine or base amino acids, sufficient amount for | pH 7 |
| Propylene glycol | 6 |
| Titanium dioxide | 8 |
| Pigments | 0.1 |
| Carboxymethyl cysteine | 1 |
| Hexachlorophene | 0.1 |
| Propyl-p-hydroxybenzoate | 0.3 |
| Sterile demineralized water, sufficient for | 100% |

This product is used in skin care.

EXAMPLE 12

Preparation of deodorants for private hygiene in the form of an aerosol foam

| | |
|---|---|
| Compound No. 10 | 3 |
| Triethanolamine or base amino acids, sufficient for | pH 7 |
| Lauryl sulfate | 30 |
| Lanolin | 2 |
| Hypoallergenic perfume | 0.2 |
| Sterile water, sufficient for | 100% |

To 90 parts of the above mixture there are used 10 parts of the following aerosol propellant in a 50/50 mixture: Freon 114 ($CClF_2CClF_2$)/Freon 12($CCl_2F_2$).

EXAMPLE 13

Protective lotion:

The following composition is prepared in % by weight:

| | |
|---|---|
| Compound No. 70 bis | 0.5 |
| Triethanolamine or base amino acids, sufficient for | pH 7 |
| Propylene glycol | 30 |
| Sterile water, sufficient for | 100% |

EXAMPLE 14

According to the method for preparing the milk of Example 1, a protective day cream having the composition in % by weight is prepared:

| | |
|---|---|
| Stearic acid | 2.00 |
| Cosbiol | 20.00 |
| Glycerol monostearate | 2.00 |
| Triethanolamine | 1.00 |
| Preservative (methyl-p-hydroxybenzoate) | 0.30 |
| Carbopol 941 | 0.30 |
| Compound 11 A | 1.00 |
| Perfume | 0.30 |
| Demineralized water, sufficient for | 100% |

This cream assures a good protection of the skin.

EXAMPLE 15

An afer-shave fluid having the composition in % by weight is prepared as follows:

| | |
|---|---|
| Compound No. 44 | 0.50 |
| Carbopol 934 | 0.25 |
| Triethanolamine | 0.25 |
| Propylene glycol | 5.00 |
| Preservative (methyl-p-hydroxybenzoate) | 0.30 |
| Perfume | 0.2 |
| Sterile demineralized water, sufficient for | 100% |

A solution of compound No. 44 obtained by dispersing said compound in one part of water and then neutralizing it with triethanolamine, is mixed with the propylene glycol. The preservative, dissolved in water, and then the perfume are added. This gel, when applied to the skin, gives the feeling of freshness.

EXAMPLE 16

A protective cream having the following composition in % by weight is prepared:

| | |
|---|---|
| Paraffin oil | 15.0 |
| Stearic acid | 5.0 |
| Triethanolamine | 2.5 |
| Cetyl alcohol | 3.0 |
| Compound No. 18 | 2.0 |
| Perfume | 0.2 |
| Preservative (methyl-p-hydroxybenzoate) | 0.3 |
| Water, sufficient for | 100% |

EXAMPLE 17

A bath product having the following composition in % by weight is prepared as follows:

| | |
|---|---|
| Propylene glycol | 8.0 |
| Isopropyl myristate | 1.0 |
| Compound No. 13 neutralized with aminomethyl propanol | 10.2 |
| Perfume | 0.2 |
| Preservative (methyl-p-hydroxybenzoate) | 0.3 |
| Water, sufficient for | 100% |

Compound No. 13 is dissolved in water after neutralization with aminomethylpropanol. Then the other above components are added thereto.

EXAMPLE 18

A bath cream having the following composition in % by weight is prepared as follows:

| | |
|---|---|
| Paraffin oil | 40.00 |
| Mixture of fatty alcohols of $C_{16}$ and $C_{18}$ (Lanette 0) | 3.00 |
| Sorbitan monostearate (Arlacel 60) | 3.00 |
| Sorbitan monolaurate (Tween 20) | 4.00 |
| Compound No. 42 | 4.00 |
| Perfume | 0.2 |
| Preservative (methyl-p-hydroxybenzoate) | 0.3 |
| Water, sufficient for | 100% |

The fatty components are melted at 75°C. Compound No. 42 is dissolved in water with the preservative and the resulting solution is then heated to 75°C. The melted components and solution of compound 42 are mixed with stirring. After cooling, the perfume is incorporated.

EXAMPLE 19

According to the same method for preparing the milk of Example 1, a regenerating night cream having the following composition in % by weight is prepared:

| | |
|---|---|
| Cetyl ether polyoxyethylene (10 moles) (BRIJ 56) | 2.00 |
| Stearyl ether polyoxyethylene (10 moles) (BRIJ 76) | 2.00 |
| Glycerin monostearate | 4.00 |
| Perhydrosqualen (Cosbiol) | 9.00 |
| Vaseline oil | 32.00 |
| Stearic acid | 2.00 |
| Compound 70 bis | 5.00 |
| Perfume | 0.30 |
| Preservative (methyl-p-hydroxybenzoate) | 0.30 |
| Triethanolamine | 0.10 |
| Demineralized water, sufficient for | 100% |

EXAMPLE 20

A regenerating lotion having the following composition in % by weight is prepared as follows:

| | |
|---|---|
| Compound No. 12 A | 2.00 |
| Rose water | 50.00 |
| Preservative (methyl-p-hydroxybenzoate) | 0.3 |
| Perfume | 0.2 |
| Sterile demineralized water, sufficient for | 100% |

The preservative is dissolved in water, then compound No. 12 A is also dissolved. The rose water and perfume are introduced therein and the whole is filtered and dyed.

EXAMPLE 21

According to the method of preparing the milk of Example 1, a cleansing base having the following composition in % by weight is prepared:

| | |
|---|---|
| Stearic acid | 2.00 |
| Vaseline oil | 20.00 |
| Glycerol monostearate | 2.00 |
| Hexadecyl alcohol | 0.50 |
| Cetyl alcohol | 0.50 |
| Triethanolamine | 1.30 |
| Preservative (methyl-p-hydroxybenzoate) | 0.30 |
| Carbopol 941 | 0.30 |
| Compound No. 16 | 1.00 |
| Perfume | 0.30 |
| Demineralized water, sufficient for | 100% |

In the above cosmetic compositions the following components employed are more precisely identified as follows:

Amerchol L 101 - Liquid, multi-sterol, non-ionic, surface-active penetrant, emollient and emulsifier. Sterols and higher alcohols are present only in their free forms. Anhydrous, oil soluble, water dispersible, practically odorless, tasteless and pale straw color.

Cosbiol - Perhydrosqualene.

Carbopol 934 - a high molecular weight carboxy vinyl polymer comprising polyacrylic acid crosslinked with 1% of a polyallyl ether of sucrose having an average of about 5.8 allyl groups for each molecule of sucrose. Carbopol 941 is similarly constituted and gives slightly less viscous solutions than Carbopol 934. See U.S. Pat. No. 3,133,865

Pur Cellin Oil - fatty acid ester with alkylated branching, having a density (20°) of 0.852 to 0.857, index of refraction (20°) - 1.444 to 1.4465, acid index of 0 to 1, ester index of 90 to 140, iodine index (Kaufman) of 0 to 1 and a congealing point of −4° to 1.0°.

Vaseline Oil - liquid petrolatum or paraffin oil.

What is claimed is:

1. A cosmetic composition for the skin comprising in an aqueous carrier a chitosan derivative consisting of randomly distributed patterns of the formulae:

(A) 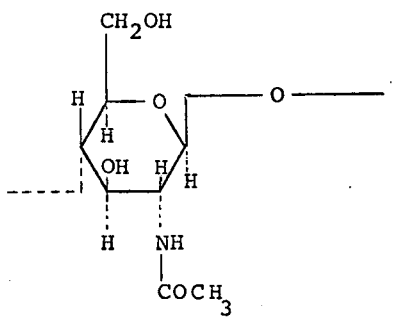

(B) 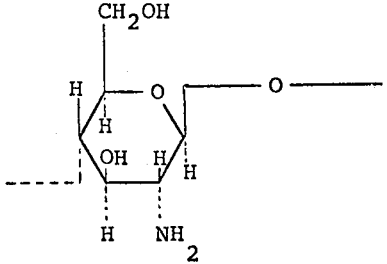 and (C) 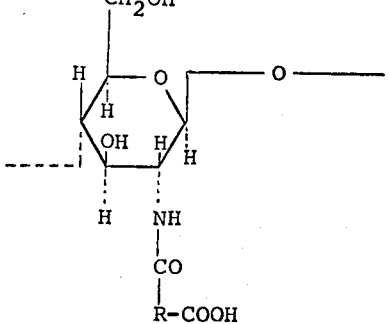

the proportions of these three patterns being, respectively, 5 to 30% for A, 5 to 40% for B and 30 to 90% for C, R representing a member selected from the group consisting of

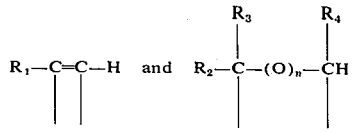

wherein $R_1$ represents a member selected from the group consisting of hydrogen and methyl, $n$ is equal to (a) O, in which case $R_2$, $R_3$ and $R_4$, each independently, represent a member selected from the group consisting of hydrogen; methyl; hydroxy; acetoxy; amino; monoalkylamino or dialkylamino, wherein the alkyl moiety of each has 1 to 12 carbon atoms and wherein each is optionally interrupted by one or more nitrogen atoms or substituted by one or more amino, hydroxyl, mercapto, carboxyl, alkylthio wherein the alkyl moiety has 1 to 8 carbon atoms and sulfonic groups; alkylthio wherein the alkyl moiety has 1 to 4 carbon atoms and carries an amino residue; and a residue of glutathion, at least one of $R_2$, $R_3$ and $R_4$ being hydrogen and radicals $R_2$ and $R_3$ being able to form together a methylene radical, and (b) 1, in which case $R_2$, $R_3$ and $R_4$ each represent hydrogen; and the salts formed by this derivative with a base selected from the group consisting of sodium hydroxide, potassium hydroxide, ammonia, lime, magnesia and alkanolamine and an acid selected from the group consisting of hydrochloric, phosphoric, acetic, lactic, tartaric and citric, said chitosan derivative being present in amounts of 0.1 − 20 percent by weight of said composition.

2. The cosmetic composition of claim 1 which also includes a thickening agent.

3. The cosmetic composition of claim 2 wherein said thickening agent is high molecular weight carboxyvinyl polymer comprising polyacrylic acid crosslinked with about 1% of polyallyl sucrose having an average of about 5.8 allyl groups for each sucrose molecule.

4. The cosmetic composition of claim 1 which also includes a fatty component.

5. The cosmetic composition of claim 1 which also includes a preservative.

6. The cosmetic composition of claim 5 wherein said preservative is methyl p-hydroxybenzoate.

7. The cosmetic composition of claim 6 which also includes a perfume.

8. The cosmetic composition of claim 1 neutralized to pH 7.

* * * * *

UNITED STATES PATENT OFFICE
CERTIFICATE OF CORRECTION

Patent No. 3,953,608   Dated April 27, 1976

Inventor(s) Guy Vanlerberghe and Henri Sebag

It is certified that error appears in the above-identified patent and that said Letters Patent are hereby corrected as shown below:

In the heading, in [30] Foreign Application Priority Data:

--April 18, 1972  Luxembourg 65,186--

Signed and Sealed this

Twenty-second Day of February 1977

[SEAL]

Attest:

RUTH C. MASON
Attesting Officer

C. MARSHALL DANN
Commissioner of Patents and Trademarks